US008975450B2

(12) United States Patent
Scates

(10) Patent No.: US 8,975,450 B2
(45) Date of Patent: Mar. 10, 2015

(54) ETHANOL AND ETHYL ACETATE PRODUCTION USING AN ACETIC ACID AND ACETIC ANHYDRIDE MIXED FEED

(71) Applicant: Celanese International Corporation, Irving, TX (US)

(72) Inventor: Mark O. Scates, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/834,120

(22) Filed: Mar. 15, 2013

(65) Prior Publication Data

US 2014/0275641 A1    Sep. 18, 2014

(51) Int. Cl.
C07C 29/14      (2006.01)
C07C 29/149     (2006.01)

(52) U.S. Cl.
CPC .................................. *C07C 29/149* (2013.01)
USPC .......................................... 568/881; 568/880

(58) Field of Classification Search
None
See application file for complete search history.

(56) References Cited

U.S. PATENT DOCUMENTS

| | | |
|---|---|---|
| 2,549,416 A | 4/1951 | Brooks |
| 3,102,150 A | 8/1963 | Hunter et al. |
| 4,107,002 A | 8/1978 | Eck et al. |
| 4,426,541 A | 1/1984 | King |
| 4,443,639 A | 4/1984 | Pesa et al. |
| 4,454,358 A | 6/1984 | Kummer et al. |
| 4,465,854 A | 8/1984 | Pond et al. |
| 4,497,967 A | 2/1985 | Wan |
| 4,517,391 A | 5/1985 | Schuster et al. |
| 4,581,473 A | 4/1986 | Polichnowski |
| 4,600,571 A | 7/1986 | McCarroll et al. |
| 4,737,318 A | 4/1988 | Ichino et al. |
| 4,880,937 A | 11/1989 | Matsushita et al. |
| 4,886,905 A | 12/1989 | Larkins, Jr. |
| 4,943,354 A | 7/1990 | Osterburg et al. |
| 4,994,608 A | 2/1991 | Torrence et al. |
| 5,001,259 A | 3/1991 | Smith et al. |
| 5,026,908 A | 6/1991 | Smith et al. |
| 5,149,680 A | 9/1992 | Kitson et al. |
| 5,227,524 A | 7/1993 | Jones |
| 5,243,095 A | 9/1993 | Roberts et al. |
| 5,414,161 A | 5/1995 | Uhm et al. |
| 5,922,911 A * | 7/1999 | Jones et al. .................... 562/893 |
| 6,232,352 B1 | 5/2001 | Vidalin |
| 6,486,366 B1 | 11/2002 | Ostgard et al. |
| 6,495,730 B1 | 12/2002 | Konishi et al. |
| 6,509,180 B1 | 1/2003 | Verser et al. |
| 7,361,794 B2 | 4/2008 | Grosso |
| 7,790,938 B2 | 9/2010 | Kawasaki et al. |
| 7,842,844 B2 | 11/2010 | Atkins |
| 7,947,746 B2 | 5/2011 | Daniel et al. |
| 7,964,379 B2 | 6/2011 | Verser et al. |
| 8,062,482 B2 | 11/2011 | Warner |
| 8,071,389 B2 | 12/2011 | Weck et al. |
| 8,080,693 B2 | 12/2011 | Chornet et al. |
| 8,232,440 B2 | 7/2012 | Holtzapple et al. |
| 8,288,596 B2 | 10/2012 | Garton et al. |
| 2011/0004034 A1 | 1/2011 | Daniel et al. |
| 2011/0190548 A1 * | 8/2011 | Jevtic et al. .................... 568/885 |
| 2011/0190552 A1 | 8/2011 | Powell et al. |
| 2011/0224462 A1 | 9/2011 | Ditzel et al. |
| 2014/0058139 A1 | 2/2014 | Powell et al. |

FOREIGN PATENT DOCUMENTS

| | | |
|---|---|---|
| CN | 1230458 | 10/1999 |
| EP | 0087870 | * 9/1983 |
| EP | 0164922 | 12/1985 |
| EP | 0104197 | 5/1986 |
| EP | 2060553 | 5/2009 |
| EP | 2072487 | 6/2009 |
| EP | 2072488 | 6/2009 |
| WO | WO 2009/009322 | 1/2009 |
| WO | WO2011/097220 | 8/2011 |
| WO | 2013070209 | * 5/2013 |

OTHER PUBLICATIONS

WO 2013070210 (Abstract, Derwent Worl Patent Index).*
International Search Report and Written Opinion for PCT/US2014/027969 mailed Jun. 30, 2014.

* cited by examiner

*Primary Examiner* — Karl J Puttlitz

(57) ABSTRACT

Ethanol production processes using a mixed feed comprising from 20 to 95 wt. % acetic acid, from 5 to 80 wt. % acetic anhydride, and from 0 to 20 wt. % esters selected from the group consisting of methyl acetate, ethyl acetate, or mixtures thereof are disclosed herein. The process comprises contacting the mixed feed with hydrogen in the vapor phase in a reactor in the presence of a catalyst comprising tin, cobalt, platinum, and combinations thereof to form a crude ethanol product having an ethanol to water molar ratio of greater than 1 and separating the crude ethanol product in one or more distillation columns to yield an ethyl acetate stream and an ethanol stream. The process may be integrated with an acetic anhydride production process to obtain further economic savings.

20 Claims, No Drawings

US 8,975,450 B2

ETHANOL AND ETHYL ACETATE PRODUCTION USING AN ACETIC ACID AND ACETIC ANHYDRIDE MIXED FEED

FIELD OF THE INVENTION

The present invention relates generally to alcohol production from mixed feed, and in particular to producing ethanol through hydrogenating a mixed feed comprising acetic acid and acetic anhydride.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of acetic acid is described in the literature. U.S. Pat. No. 5,149,680 describes a catalyst composition comprising an alloy of at least one noble metal of Group VIII of the Periodic Table and at least one metal capable of alloying with the Group VIII noble metal, admixed with a component comprising at least one of the metals rhenium, tungsten or molybdenum, used for producing an alcohol and/or a carboxylic acid ester by reacting hydrogen with a carboxylic acid or anhydride thereof. Ethanol may also be prepared by hydrogenating acetic acid under superatmospheric pressure and at elevated temperatures by a process described in U.S. Pat. No. 4,517,391 wherein a predominantly cobalt-containing catalyst is used and acetic acid and hydrogen are passed through the reactor, at from 210° C. to 330° C. and under from 10 to 350 bar, under conditions such that a liquid phase in not formed during this procedure.

U.S. Pat. No. 6,495,730 discloses a catalyst for hydrogenating a carboxylic acid, comprising an activated carbon having carried thereon an active metal species comprising ruthenium and tin, wherein the activated carbon, prior to having carried thereon the active metal species, exhibits specific pore characteristics.

U.S. Pat. No. 5,243,095 process for hydrogenating aldehydes, ketones, carboxylic acids, and carboxylic acid esters to alcohols comprising contacting the aldehydes, ketones, acids or esters with hydrogen and a catalyst under catalytic hydrogenation conditions the improvement comprising using a catalyst in powdered form comprising copper, iron, aluminum and manganese wherein the atomic ratio of copper to iron is at least 1:1.

U.S. Pat. No. 4,443,639 discloses a process for the vapor phase hydrogenation of carboxylic acids to yield their corresponding alcohols in the presence of steam and a catalyst comprising the mixed oxides of ruthenium, at least one of cobalt, nickel, and optionally one of cadmium, zinc, copper, iron, rhodium, palladium, osmium, iridium and platinum.

Acetic acid is typically produced by carbonylation of methanol as described in U.S. Pat. Nos. 5,026,908, 5,001,259, and 4,994,608. Acetic acid may also be produced from fermentation as described in U.S. Pat. No. 6,509,180. Another route to acetic anhydride, typically under anhydrous conditions, involves carbonylating methyl acetate to acetic anhydride as described in U.S. Pat. No. 5,922,911. Acetic acid may be co-produced with acetic anhydride. The entire contents and disclosures of which are hereby incorporated by reference.

Acetic anhydride may be reduced, under hydrogenation, to a variety of products. EP0164922 describes a process for the hydrogenation of carboxylic acid derivatives such as carboxylic anhydrides or alkylidene dicarboxylates. The catalyst used to effect the hydrogenation process comprises (1) a Group VIII metal catalyst e.g. ruthenium or rhodium, in the metallic state and (2) a strong acid promoter. The process is useful for hydrogenating acetic anhydride, propionic anhydride and ethylidene diacetate at superatmospheric pressure. When acetic anhydride is hydrogenated, the main products are ethyl acetate, ethylidene diacetate and acetic acid. U.S. Pat. No. 4,581,473 discloses a process for the preparation of ethylidene diacetate by hydrogenating acetic anhydride in the presence of a homogeneous rhodium catalyst, methyl iodide and lithium iodide. U.S. Pat. No. 4,886,905 discloses a process for the preparation of ethylidene diacetate and/or ethyl acetate by hydrogenating acetic anhydride in the presence of a homogeneous ruthenium catalyst, methyl iodide and, optionally, lithium iodide. The process can also be utilized to hydrogenate mixtures of acetic anhydride and ethylidene diacetate to produce ethyl acetate.

To produce ethanol from acetic anhydride, U.S. Pat. No. 4,497,967 discloses an integrated process for the preparation of ethanol from methanol, carbon monoxide and hydrogen feedstock. The process features the steps of esterifying methanol and acetic acid to form methyl acetate, carbonylating the methyl acetate to form acetic anhydride, esterifying acetic anhydride with a lower aliphatic alcohol in an anhydrous zone to form the corresponding aliphatic acetate, hydrogenating the aliphatic acetate in a second anhydrous zone to form ethanol and the corresponding aliphatic alcohol, and separating the formed ethanol stream into an ethanol product stream and/or aliphatic alcohol recycle stream, which is recycled to react with acetic anhydride.

The need remains for improved processes for efficient ethanol production from acetic anhydride on a commercially feasible scale.

SUMMARY OF THE INVENTION

In a first embodiment, the present invention is directed to a process of producing ethanol comprising providing a mixed feed comprising from 20 to 95 wt. % acetic acid, from 5 to 80 wt. % acetic anhydride, and from 0 to 20 wt. % esters selected from the group consisting of methyl acetate, ethyl acetate, or mixtures thereof; contacting the mixed feed with hydrogen in the vapor phase in a reactor in the presence of a catalyst having at least one metal selected from the group consisting of tin, cobalt, platinum, and combinations thereof to foam a crude ethanol product having an ethanol to water molar ratio of greater than 1; and separating the crude ethanol product in one or more distillation columns to yield a first stream comprising ethyl acetate and a second stream comprising ethanol. The catalyst may further comprise at least one metal or silicate or oxides thereof from the group consisting of calcium, magnesium, tungsten, molybdenum, or vanadium. Preferably, the catalyst is substantially free of rhodium, ruthenium, or copper. The crude ethanol product preferably comprises less than 25 wt. % water. In one embodiment, if the crude ethanol product contains water, the composition may include from 30 to 90 wt. % ethanol, 1 to 25 wt. % water, 0 to 50 wt. % acetic acid, 0 to 10 wt. % acetic anhydride, and 0.1 to 25 wt. % ethyl acetate. In one embodiment, if the crude ethanol product contains no water, the composition may include from 30 to 90 wt. % ethanol, 0 wt. % water, 0 to 50 wt. % acetic acid, 0.01 to 10 wt. % acetic anhydride, and 0.1 to 25 wt. % ethyl acetate.

In another embodiment, the present invention is directed to a process of producing ethanol comprising providing a mixed feed comprising from 20 to 50 wt. % acetic acid, from 35 to 80 wt. % acetic anhydride, and from 0 to 20 wt. % esters selected from the group consisting of methyl acetate, ethyl acetate, or mixtures thereof; contacting the mixed feed with hydrogen in the vapor phase in a reactor in the presence of a catalyst having at least one metal selected from the group consisting of tin, cobalt, platinum, and combinations thereof to form a crude ethanol product, preferably the crude ethanol product has an ethanol to water molar ratio of greater than 1; and separating the crude ethanol product in one or more distillation columns to yield a first stream comprising ethyl acetate and a second stream comprising ethanol.

In a second embodiment, the present invention is directed to an integrated process for producing ethanol comprising carbonylating methyl acetate to form a mixed feed comprising acetic acid and acetic anhydride; contacting the mixed feed with hydrogen in a reactor in the vapor phase in the presence of a catalyst having at least one metal selected from the group consisting of tin, cobalt, platinum, and combinations thereof to form a crude ethanol product having an ethanol to water molar ratio of greater than 1; and separating the crude ethanol product in one or more distillation columns to yield a first stream comprising ethyl acetate and a second stream comprising ethanol. The mixed feed may comprise from 20 to 95 wt. % acetic acid, e.g. from 20 to 50 wt. % acetic acid, from 5 to 80 wt. % acetic anhydride, e.g. from 35 to 80 wt. % acetic anhydride, and from 0 to 20 wt. % esters selected from the group consisting of methyl acetate, ethyl acetate, or mixtures thereof.

DETAILED DESCRIPTION OF THE INVENTION

The present invention relates to processes for producing ethanol from a mixed feed comprising acetic acid and acetic anhydride. The mixed feed is contacted with hydrogen to produce a crude ethanol product. Due to the presence of acetic anhydride the crude ethanol product may have an ethanol to water molar ratio of greater than 1, e.g., greater than 1.2 or greater than 1.5. Assuming complete conversion and selectivity to ethanol, the maximum water concentration in the crude ethanol product is less than 25 wt. %. This allows the production of ethanol with reduced amounts of water that advantageously improves the economics to produce ethanol on a commercial scale. In addition, the mixed feed may be obtained from a methyl acetate carbonylation process without having to separate acetic acid and acetic anhydride. This may lead to further efficiencies when integrating with a carbonylation process. In another embodiment, the mixed feed may be obtained from contacting a vinyl acetate based polymer or copolymer (PVAc or EVAc) with a base and methanol. This produces methyl acetate that may be carbonylated to form the mixed feed. This may lead to further efficiencies when integrating with a vinyl acetate based polymer process.

Acetic anhydride conventionally produces a variety of undesirable products under hydrogenation conditions when used as a sole feed source. The undesirable products that are formed when acetic anhydride is used alone include ethyl acetate, acetic acid, ethylidene diacetate, and mixtures thereof. The present invention provides an advantage by using a mixed feed of acetic acid and acetic anhydride. This allows acetic anhydride to produce ethanol through intermediates. Under theoretical conditions, acetic acid alone produces an equal molar ratio of ethanol and water. The water of the reaction must be separated to recover a useful ethanol product, especially for fuels. With the presence of acetic anhydride in the mixed feed, the water may be consumed in the reactor and reduces the amount of water in the crude ethanol product. The present invention advantageously produces an excess molar amount of ethanol relative to water to reduce the energy requirements needed to remove water from the ethanol product. The following primary reactions occur when the mixed feed and hydrogen are fed to the reactor.

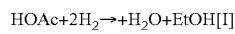
HOAc+2H$_2$→+H$_2$O+EtOH[I]

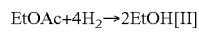
EtOAc+4H$_2$→2EtOH[II]

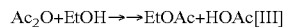
Ac$_2$O+EtOH→→EtOAc+HOAc[III]

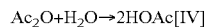
Ac$_2$O+H$_2$O→2HOAc[IV]

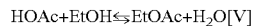
HOAc+EtOH⇌EtOAc+H$_2$O[V]

Without being bound by theory, the initial acetic acid fed to the reactor is reduced to an equal molar amount of ethanol and water in Reaction I. Due to the presence of water formed in Reaction I, the reactor operates under hydrous conditions. Acetic anhydride reacts with ethanol in Reaction III to produce ethyl acetate and acetic acid. Reaction III is not easily reversible. Ethyl acetate and acetic acid may be reduced to ethanol by Reactions I and II. The presence of water may suppress Reaction III. Acetic anhydride may be hydrolyzed in Reaction IV to produce two moles of acetic acid that can be converted to ethanol in Reaction I. The rate of Reaction IV is faster than Reaction III and helps to complete the conversion of acetic anhydride. The hydrolysis is potentially a violent reaction that may be accelerated in the presence of mineral acid, such as nitric acid, perchloric acid, and sulfuric acid. Thus, to reduce the potential for flammability the reactor is free of mineral acids. Acetic acid may also be esterified through an equilibrium reaction in Reaction V. Any ethyl acetate produced from this esterification may be reduced to ethanol.

In one embodiment, the mixed feed comprises from 20 to 95 wt. % acetic acid, e.g., from 35 to 75 wt. % acetic acid, from 5 to 80 wt. % acetic anhydride, e.g., from 10 to 50 wt. % acetic anhydride, and optionally from 0 to 20 wt. % esters, e.g., from 0 to 10 wt. % esters. In term of molar ratios of acetic anhydride, and the mixed feed may have an acetic acid to acetic anhydride molar ratio from 15:1 to 1:15, e.g., from 10:1 to 1:10.

In another embodiment, the mixed feed comprises from 20 to 50 wt. % acetic acid, e.g., from 25 to 40 wt. % acetic acid, from 35 to 80 wt. % acetic anhydride, e.g., from 50 to 70 wt. % acetic anhydride, and optionally from 0 to 20 wt. % esters, e.g., from 0 to 10 wt. % esters. In one embodiment, there may be an excess molar amount of acetic anhydride, and the mixed feed may have an acetic acid to acetic anhydride molar ratio from 1:7 to 1:1.5, e.g., from 1:2 to 1:4.

The mixed feed may also comprise from 10 to 1000 wppm ethylidene diacetate. Other components such as acetaldehyde and water may be present in the mixed feed in amounts of less than 5 wt. %. The esters may include methyl acetate, ethyl acetate, or mixtures thereof. Any methyl acetate that may be present in the mixed feed may be from the methyl acetate carbonylation process. However, methyl acetate may also carry over undesirable amounts of methyl iodide. Ethyl acetate may be co-produced in the reactor and recycled to the mixed feed.

The reactions may be carried out in either the liquid phase or vapor phase in the same reaction vessel. Preferably, the reaction is carried out in the vapor phase under the following conditions. The reaction temperature may range from 175° C. to 325° C., e.g., from 225° C. to 300° C., or from 250° C. to 300° C. The pressure may range from 100 kPa to 3000 kPa, e.g., from 150 kPa to 2300 kPa, or from 300 kPa to 2000 kPa. The reactants may be fed to the reactor at a gas hourly space velocity from 50 $hr^{-1}$ to 50,000 $hr^{-1}$, e.g., from 500 $hr^{-1}$ to 30,000 $hr^{-1}$, or from 1000 $hr^{-1}$ to 6500 $hr^{-1}$.

Theoretically the reduction reactions of acetic acid and ethyl acetate consume two moles and four moles of hydrogen respectively, but it is preferred to react acetic acid and ethyl acetate with an excess of hydrogen. Because acetic acid is fed to the reactor in the mixed feed, the molar ratio of hydrogen to acetic acid in the mixed feed stream may vary from 25:1 to 1:1, e.g., from 20:1 to 1:1, or from 18:1 to 2:1. Most preferably, the molar ratio of hydrogen to acetic acid is greater than 2:1, e.g., greater than 4:1 or greater than 8:1. Based on the ethyl acetate formed in the reaction, the molar ratio of hydrogen to ethyl acetate may be greater than 5:1, e.g., greater than 10:1 or greater than 15:1.

The process of the present invention preferably has high conversions of acetic anhydride and acetic acid. For purposes of the present invention, the term "conversion" refers to the amount of reactant, acetic acid or acetic anhydride, in the mixed feed that is converted to another compound. Conversion is expressed as a percentage based on acetic acid or acetic anhydride in the mixed feed. In one embodiment, the acetic anhydride conversion may be very high relative to the acetic acid conversion and the acetic anhydride conversion may be greater than 90%, e.g. greater than 95% or greater than 99%. The acetic acid conversion may vary and is at least 20%, more preferably at least 60%, at least 75%, at least 80%, at least 90%, at least 95% or at least 99%. Typically acetic anhydride approaches 100% and acetic acid conversion is less than acetic anhydride conversion. Because ethyl acetate may be produced in the reactor and may be present in the mixed feed in some embodiments, it is also preferably to have an ethyl acetate conversion that limits the net increase of ethyl acetate in the crude ethanol product, e.g., 0% conversion. In some embodiments, the present invention may operate at an ethyl acetate conversions of at least 0%, e.g., at least 5%, at least 10%, at least 15%, at least 20%, or at least 35%.

Selectivity is expressed as a mole percent based on converted reactants, i.e. acetic acid and acetic anhydride. It should be understood that acetic anhydride does not directly convert ethanol, but forms ethanol through intermediates. For example, if 60 mole % of the converted reactants is converted to ethanol, we refer to the ethanol selectivity as 60%. For purposes of the present invention, the total selectivity is based on the combined converted acetic acid and acetic anhydride. Preferably, total selectivity to ethanol is at least 80%, e.g., at least 85% or at least 90%. Some embodiments also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the reactants passed over the catalyst are converted to alkanes, which have little value other than as fuel.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. For purposes of the present invention, the ethanol to water molar ratio will be greater than 1, and the ethanol concentration are selected to satisfy this molar ratio. The composition in Table 1 may include others that are not separately identified, such as, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) |
|---|---|---|---|
| Ethanol | 30 to 90 | 35 to 85 | 50 to 80 |
| Acetic Acid | 0 to 50 | 0 to 40 | 0.1 to 35 |
| Acetic Anhydride | 0 to 10 | 0 to 5 | 0 to 3 |
| Water | 1 to 25 | 5 to 25 | 5 to 20 |
| Ethyl Acetate | 0.1 to 25 | 1 to 20 | 5 to 18 |
| Acetaldehyde | 0 to 10 | 0 to 3 | 0.1 to 3 |

Acetic hydride generally cannot co-exist with water and is quickly converted as shown in Reaction IV. In one preferred embodiment, when crude ethanol product composition contains any acetic anhydride, the water concentration will effectively be zero. For example, when water is 0 wt. % in Table 1, then acetic anhydride may be from 0.01 to 10 wt. %, e.g., from 0.1 to 5 wt. % or from 0.1 to 3 wt. %. Thus, the crude ethanol product may comprise from 30 to 90 wt. % ethanol, 0 wt. % water, 0 to 50 wt. % acetic acid, 0.01 to 10 wt. % acetic anhydride, and 0.1 to 25 wt. % ethyl acetate.

The mixed feed may be vaporized at the reaction temperature and pressure, following which the vaporized mixed feed may be introduced to a reactor with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of any components in the mixed fed, such as acetic anhydride or acetic acid. In one embodiment, the mixed feed may be vaporized at the boiling point of acetic acid at the particular pressure, and then the vaporized feed may be superheated to the reactor inlet temperature. In another embodiment, the mixed feed is mixed with other gases before vaporizing, followed by heating the mixed vapors up to the reactor inlet temperature. Preferably, the mixed feed is transferred to the vapor state by passing hydrogen and/or recycle gas through the mixed feed at a temperature at or below the boiling point of the mixed feed at reaction temperature and pressure, followed by superheating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of acetic acid to ethanol and a second bifunctional catalyst is employed in the second stage for converting unreacted acetic acid to ethanol as well as converting byproduct ester, e.g., ethyl acetate, to ethanol.

The reactions for converting acetic acid directly to ethanol and acetic anhydride through intermediates to ethanol are conducted in the presence of a catalyst. In one embodiment, the catalyst comprises cobalt, tin, platinum and combinations thereof. Preferably, the catalyst comprises at least two of the preceding metals. The catalyst may also comprise a metal, oxide or silicate of calcium, magnesium, tungsten, molybdenum, vanadium, and combinations thereof. In one embodiment, the catalyst does not comprise any, and is substantially free of rhodium, ruthenium, or copper. The catalyst may be support on a suitable support as described herein.

The catalyst may comprise platinum in an amount from 0.05 to 3 wt. %, e.g. from 0.1 to 1.5 wt. %, based on the total weight of the catalyst. The catalyst may comprise from cobalt in an amount from 0.5 to 20 wt. %, e.g., from 4.1 to 20 wt. %. The catalyst may comprise tin in an amount from 0.5 to 20 wt. %, e.g., from 0.5 to 3.5 wt. %. The total weight of cobalt, tin, and platinum may be less than 25 wt. %.

In some embodiments, the catalyst may also include an additional precious metal selected, for example, from the group consisting of rhenium, palladium, osmium, iridium and gold. The precious metal may be in elemental form or in molecular form, e.g., an oxide of the precious metal. The catalyst comprises such precious metals in an amount from 0.05 to 10 wt. %, e.g. from 0.1 to 5 wt. %, based on the total weight of the catalyst. In another embodiment, the catalyst may comprise one or more secondary metals selected from the group consisting of iron, nickel, titanium, zinc, chromium, lanthanum, cerium, or manganese. The catalyst comprises such secondary metals in an amount from 0.1 to 25 wt. %, e.g., from 0.5 to 15 wt. %, based on the total weight of the catalyst.

Preferred metal combinations for some exemplary catalyst compositions include platinum/tin, platinum/cobalt, tin/cobalt, platinum/tin/cobalt, platinum/tin/palladium, platinum/tin/nickel, platinum/tin/iron, platinum/cobalt/palladium, platinum/cobalt/nickel, platinum/cobalt/iron, tin/cobalt/palladium, tin/cobalt/nickel, tin/cobalt/iron, platinum/tin/cobalt/palladium, platinum/tin/cobalt/nickel, or platinum/tin/cobalt/iron. Additional combinations of metals may be possible for the present invention and the number of metals on the catalyst is not limited.

The catalysts of the present invention comprise a suitable support material, preferably a modified support material. In one embodiment, the support material may be an inorganic oxide. In one embodiment, the support material may be selected from the group consisting of silica, alumina, titania, silica/alumina, pyrogenic silica, high purity silica, zirconia, carbon (e.g., carbon black or activated carbon), zeolites and mixtures thereof. Preferably, the support material comprises a silicaceous support material such as silica, pyrogenic silica, or high purity silica. The support material comprises the balance of the catalyst and may be present in an amount from 25 wt. % to 99 wt. %, e.g., from 30 wt. % to 98 wt. %, based on the total weight of the catalyst.

In preferred embodiments, the support material comprises a silicaceous support material, e.g., silica, having a surface area of at least 50 $m^2/g$, e.g., at least 100 $m^2/g$, or at least 150 $m^2/g$. In terms of ranges, the silicaceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 250 $m^2/g$. For purposes of the present specification, surface area refers to BET nitrogen surface area, meaning the surface area as determined by ASTM D6556-04, the entirety of which is incorporated herein by reference.

The preferred silicaceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

The support material preferably comprises a support modifier. A support modifier may adjust the acidity of the support material. In one embodiment, a support modifier comprises at least one metal or silicate or oxides thereof from the group consisting of calcium, magnesium, tungsten, molybdenum, or vanadium. In one embodiment, the support modifiers are present in an amount from 1 wt. % to 40 wt. %, e.g., from 2 wt. % to 30 wt. %, from 5 wt. % to 25 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acid sites may also catalyze the reactions of acetic anhydride with ethanol or water. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In one embodiment, the support modifier is acidic may also include those selected from the group consisting of $WO_3$, $MoO_3$, $V_2O_5$, $VO_2$, $V_2O_3$, $Nb_2O_5$, $Ta_2O_5$, FeO, $Fe_3O_4$, $Fe_2O_3$, $Cr_2O_3$, $MnO_2$, $TiO_2$, $ZrO_2$, $Nb_2O_5$, $Ta_2O_5$, $Al_2O_3$, and $Bi_2O_3$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $MO_9O_{26}$, $MO_8O_{23}$, $MO_5O_{14}$, $MO_{17}O_{47}$, $MO_4O_{11}$, or $MoO_2$. In one embodiment, the tungsten oxide may be cubic tungsten oxide ($H_{0.5}WO_3$).

In some embodiments, the acidic support modifier comprises a mixed metal oxide comprising cobalt, tin, or both, and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, cobalt molybdate, cobalt vanadate, cobalt niobate, and cobalt tantalate. In one embodiment, the catalyst does not comprise and is substantially free of tin tungstate.

In one embodiment, the catalyst comprises from 0.25 to 1.25 wt. % platinum, from 1 to 10 wt. % cobalt, and from 1 to 10 wt. % tin on a silica or a silica-alumina support material. The cobalt and tin may be disposed on the support material and may be part of the modified support. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group JIB metal oxides, (vi) Group IIB metal metasilicates, (vii) Group IIIB metal oxides, (viii) Group IIIB metal metasilicates, and mixtures thereof. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

In one exemplary embodiment, the catalyst comprises from 0.25 to 1.25 wt. % platinum and 0.25 to 3 wt. % tin. These preferred active metals are on a silica support. Preferably, the silica support also comprises a support modifier such as $CaSiO_3$.

In other embodiments, the silica support may have a combination of calcium and tungsten with at least one of tin, cobalt, platinum, or combinations thereof.

In an integrated process, methyl acetate may be carbonylated to produce acetic anhydride or a mixture of acetic acid and acetic anhydride. It is preferred to integrate processes that co-produce acetic acid and acetic anhydride because the separation of these components may be eliminated. Acetic anhydride may also be obtained from carbonylating dimethyl ether or mixtures of dimethyl ester and methyl acetate. An exemplary acetic anhydride production process is described in U.S. Pat. No. 4,374,070, the disclosure of which is incorporated by reference in its entirety. Acetic anhydride generally is prepared by the carbonylation of methyl acetate in the presence of a homogeneous Group VIII catalyst, such as rhodium or nickel. An iodide promoter, such as lithium iodide, may also be used. The carbonylation may be accomplished in the liquid phase with a rhodium/iodide catalyst system promoted with ligands such as lithium, phosphines, or picolines. The acetic anhydride carbonylation is typically carried out under anhydrous conditions. Heterogeneous catalysts may also be used in some embodiments, such as those described in U.S. Pat. No. 4,328,125, the disclosure of which is incorporated by reference in its entirety.

In some integrated processes, acetic anhydride and acetic acid may be co-produced by carbonylating methyl acetate, as described in U.S. Pat. No. 6,541,666, the disclosure of which is incorporated by reference in its entirety. The process may comprise introducing a carbonylatable feedstock comprising methyl acetate and/or dimethyl ether and optionally also comprising methanol and/or water, to a carbonylation reactor in which there is maintained a liquid reaction composition comprising acetic anhydride, acetic acid, rhodium carbonylation catalyst, alkyl iodide co-catalyst and an iodide salt promoter consisting essentially of an alkali metal iodide and/or alkaline earth metal iodide, contacting said carbonylatable feedstock with carbon monoxide in said liquid reaction composition to produce acetic anhydride and acetic acid, and introducing to the carbonylation reactor methyl formate and/or formic acid in the range from 0.1 to 20% by weight of the total feed of liquid components to the reactor.

In one embodiment, methyl acetate may be obtained by alcoholysis of vinyl acetate polymers and co-polymer, such as polyvinyl acetate (PVAc) and ethylene-vinyl acetate (EVOH). A suitable alcoholysis for producing a methyl acetate stream is described in U.S. Pat. No. 7,906,680, the entire contents and disclosure of which is hereby incorporated by reference. The stream may comprise methyl acetate in an amount of 5 wt. % to 95 wt. %, e.g., 70 wt. % to 90 wt. % and methanol in an amount of 5 wt. % to 95 wt. %, e.g., 5 wt. % to 40 wt. %, based on the total weight of the stream. The methyl acetate stream may be used as the feed stream to the carbonylation process.

In the process of the present invention the carbonylatable feedstock comprises methyl acetate and/or dimethyl ether and optionally, also comprises methanol and/or water. Acetic anhydride is produced by the carbonylation of methyl acetate and/or dimethyl ether. Acetic acid is produced from methanol, water, methyl formate and/or formic acid. Thus the proportions of acetic anhydride and acetic acid produced are dependent upon the relative amounts of these components of the feedstock. It is important that the amount of methanol, water, methyl formate and/or formic acid should not be so large that the amount of acetic anhydride produced is insufficient to maintain a concentration of acetic anhydride in the liquid reaction composition. Suitable carbonylatable feedstocks include methyl acetate/methanol mixtures, dimethyl ether/methanol mixtures and methyl acetate/methanol/water mixtures.

In one embodiment, the amount of methyl formate and/or formic acid introduced into the carbonylation reactor may range from 0.1 to 20% by weight of the total feed of liquid components to the reactor, e.g., from 0.1 to 10%, provided that the amount of methanol, water, methyl formate and/or formic acid is not so great that there is no acetic anhydride maintained in the liquid reaction composition in the reactor.

The carbonylation of methyl acetate may be performed at a temperature in the range from 100° C. to 310° C., e.g., 150° C. to 210° C., and at a pressure in the range from 0.1 MPa to 10 MPa, e.g., from 1 to 5 MPa.

Methyl acetate, acetic acid and acetic anhydride are present in the liquid reaction composition maintained in the carbonylation reactor. The concentration of methyl acetate in the liquid reaction composition may be in the range from 1 to 30 wt. %, e.g., from 5 to 30 wt. %. The concentration of acetic acid in the liquid reaction composition may be in the range from 0.1 to 50 wt. % and acetic anhydride may be in the range from 0.1 to 30 wt. %.

The acetic acid and acetic anhydride product may be recovered from the carbonylation reactor, by continuously removing a portion of the liquid reaction composition from the carbonylation reactor, recovering the acetic acid and acetic anhydride products therefore and recycling the remaining components to the carbonation reactor. The withdrawn liquid reaction composition may be passed with or without the addition of heat to a separation zone from which a vapor fraction containing the acetic acid and acetic anhydride product is separated from a liquid fraction comprising rhodium carbonylation catalyst and alkali/alkaline earth metal iodide salt. The liquid fraction may be returned to the carbonylation reactor. One or more evaporators may be used to separate the liquid fraction prior to returning the catalyst to the carbonylation reactor. Suitable evaporators may be selected from the group consisting of single stage flashers, distillation towers, short-path distillation, thin film evaporators, rising film evaporators, falling film evaporators, short tube vertical evaporators, forced circulation evaporators and combinations thereof. The acetic acid and acetic anhydride are recovered from the vapor fraction in one or more separation stages, with the other light components such as methyl acetate, alkyl iodide and acetic acid being recycled to the carbonylation reactor. It is preferred to remove methyl acetate from the mixed feed because this also reduced the methyl iodide concentration in the mixed feed. Preferably there is no distillation stage to separate acetic acid from acetic anhydride. Thus, a mixed feed may be advantageously produced from the methyl acetate carbonylation without intensive energy requirements.

Carbon monoxide used in the methyl acetate carbonylation is preferably at least 95% pure, e.g., at least 97% pure. Common impurities include, but are not limited to, hydrogen, carbon dioxide, nitrogen, noble gases and lower alkanes. The rhodium catalyst requires hydrogen to enhance rate and maintain catalyst stability. Thus, if the carbon monoxide source is deficient in hydrogen, additional hydrogen may be fed to the reactor.

Carbon monoxide may be obtained from a syngas source. The syngas source may be derived from any suitable source including natural gas, petroleum, coal, biomass, and so forth. In some embodiments, some or all of the raw materials for the above-described process may be derived partially or entirely from syngas. For example, the acetic acid may be formed from methanol and carbon monoxide, both of which may be derived from syngas. Methyl acetate may be produced by esterifying acetic acid and methanol. The syngas may be formed by partial oxidation reforming or steam reforming, and the carbon monoxide may be separated from syngas. Similarly, hydrogen that is used in the step of hydrogenating the acetic acid to form the crude ethanol stream may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Black liquor, which is an aqueous solution of lignin residues, hemicellulose, and inorganic chemicals, may also be used as a biomass source. Biomass-derived syngas has a detectable $^{14}C$ isotope content as compared to fossil fuels such as coal or natural gas.

Conversion of methyl acetate in the carbonylation reactor is preferably at least 60%, e.g., at least 75%, with high selectivities to acetic anhydride of at least 80%, e.g., at least 95%. An ethanol product may be recovered from the crude ethanol product produced by the reactor may be recovered using several different techniques such as using one or more distillation columns. Any ethyl acetate produced in the reaction may be recycled to the mixed feed and returned In another embodiment, acetic anhydride may be produced using a ketene-based process. This production route is based on the thermal dehydration of acetic acid to ketene at temperatures of less than 800° C. and subsequent reaction of the ketene with additional acetic acid to form acetic anhydride. The first dehydrating reaction proceeds in the presence of an alkyl phosphate, such as a triethyl phosphate. In addition, acetic anhydride may also be produced from oxidation of acetaldehyde.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. Due to the reaction of water and acetic acid, the present invention may obtain a dry ethanol product, such as anhydrous ethanol, with reduced separation. In one embodiment, a dry ethanol product the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

I claim:

1. A process for producing ethanol comprising:
   a) providing a mixed feed comprising from 20 to 95 wt. % acetic acid, from 5 to 80 wt. % acetic anhydride, from 10 wppm to 1000 wppm ethylidene diacetate, and from 0 to 20 wt. % ester esters selected from the group consisting of methyl acetate, ethyl acetate, or mixtures thereof;
   b) contacting the mixed feed with hydrogen in the vapor phase in a reactor in the presence of a catalyst having at least one metal selected from the group consisting of tin, cobalt, platinum, and combinations thereof to form a crude ethanol product comprising 30 to 90 wt. % ethanol, 0 wt. % water, 0 to 50 wt. % acetic acid, 0.01 to 10 wt. % acetic anhydride, and 0.1 to 25 wt. % ethyl acetate; and
   c) separating the crude ethanol product in one or more distillation columns to yield a first stream comprising ethyl acetate and a second stream comprising ethanol.

2. The process of claim 1, wherein the reactor is operated at a temperature from 175° C. to 325° C. and a pressure from 100 kPa to 3000 kPa.

3. The process of claim 1, wherein the hydrogenating step b) is carried out at a molar ratio of hydrogen to acetic acid from 1:1 to 1:25.

4. The process of claim 1, wherein the conversion of acetic acid is greater than 30%.

5. The process of claim 1, wherein the conversion of acetic hydride is greater than 90%.

6. The process of claim 1, wherein total selectivity to ethanol from acetic acid and acetic anhydride is greater than 80%.

7. The process of claim 1, wherein the mixed feed has a molar ratio of acetic acid to acetic anhydride of 15:1 to 1:15.

8. The process of claim 1, wherein the acetic acid and acetic anhydride are derived from synthesis gas, and wherein the synthesis gas is derived from a carbonaceous material selected from the group consisting of oil, coal, natural gas and biomass.

9. The process of claim 1, wherein the catalyst further comprises at least one metal or silicate or oxides thereof from the group consisting of calcium, magnesium, tungsten, molybdenum, or vanadium.

10. The process of claim 1, wherein the catalyst is substantially free of rhodium, ruthenium, or copper.

11. An integrated process for producing ethanol comprising:
    a) carbonylating a stream comprising methyl acetate to form a mixed feed comprising acetic acid and acetic anhydride;
    b) contacting the mixed feed with hydrogen in a reactor in the vapor phase in the presence of a catalyst having at least one metal selected from the group consisting of tin, cobalt, platinum, wherein the catalyst is substantially free of rhodium, ruthenium, or copper, and combinations thereof to form a crude ethanol product comprising 30 to 90 wt. % ethanol, 0 wt. % water, 0 to 50 wt. % acetic acid, 0.01 to 10 wt. % acetic anhydride, and 0.1 to 25 wt. % ethyl acetate; and
    c) separating the crude ethanol product in one or more distillation columns to yield a first stream comprising ethyl acetate and a second stream comprising ethanol.

12. The integrated process of claim 11, further comprising removing lights ends comprising methyl acetate from the mixed feed.

13. The integrated process of claim 11, wherein the mixed feed is not subjected to separation process to remove the acetic acid from the acetic anhydride.

14. The integrated process of claim 11, further comprising esterifying methanol and acetic acid to produce the methyl acetate and introducing the methyl acetate to the carbonylating step.

15. The integrated process of claim 14, wherein the acetic acid is formed by carbonylating methanol.

16. The integrated process of claim 11, wherein the methanol is formed from synthesis gas, and wherein the synthesis gas is derived from a carbonaceous material selected from the group consisting of oil, coal, natural gas and biomass.

17. The integrated process of claim 11, wherein the mixed feed comprises from 20 to 95 wt. % acetic acid, from 5 to 80 wt. % acetic anhydride, from 10 wppm to 1000 wppm ethylidene diacetate, and from 0 to 20 wt. % ester esters selected from the group consisting of methyl acetate, ethyl acetate, or mixtures thereof.

18. The integrated process of claim 11, wherein the step b) is performed at a temperature from 175° C. to 325° C. and a pressure from 100 kPa to 3000 kPa.

19. The integrated process of claim 11, wherein the step b) is carried out at a molar ratio of hydrogen to acetic acid from 1:1 to 1:25.

20. The integrated process of claim 11, wherein the conversion of acetic acid is greater than 30% and wherein the conversion of acetic hydride is greater than 90%.

* * * * *